(12) United States Patent
Carrión et al.

(10) Patent No.: US 6,383,795 B1
(45) Date of Patent: May 7, 2002

(54) EFFICIENT PURIFICATION OF ADENOVIRUS

(75) Inventors: Miguel E. Carrión, Rockville; Marilyn Menger, Derwood; Imre Kovesdi, Rockville, all of MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/296,962

(22) Filed: Apr. 22, 1999

Related U.S. Application Data (60) Provisional application No. 60/082,628, filed on Apr. 22, 1998.

(51) Int. Cl.[7] .................................................. C12N 7/02
(52) U.S. Cl. ........................................... 435/239; 435/5
(58) Field of Search ...................... 435/239, 5

(56) References Cited

U.S. PATENT DOCUMENTS

| | | |
|---|---|---|
| 5,019,270 A | 5/1991 | Afeyan et al. |
| 5,228,989 A | 7/1993 | Afeyan et al. |
| 5,268,097 A | 12/1993 | Girot et al. |
| 5,384,042 A | 1/1995 | Afeyan et al. |
| 5,552,041 A | 9/1996 | Afeyan et al. |
| 5,605,623 A | 2/1997 | Afeyan et al. |
| 5,672,276 A | 9/1997 | Girot et al. |
| 5,837,520 A | * 11/1998 | Shabram et al. ............ 435/239 |

FOREIGN PATENT DOCUMENTS

| | | | |
|---|---|---|---|
| EP | 0 213 719 | 3/1987 | |
| EP | 764446 | * 3/1997 | .......... A61K/39/23 |
| WO | WO 96/27677 | 9/1996 | |
| WO | 97/08298 | * 3/1997 | ............ C12N/7/02 |
| WO | WO 98/00524 | 1/1998 | |
| WO | 98/00524 | * 1/1998 | ............ C12N/7/02 |
| WO | WO00/40702 A1 | 7/2000 | |
| WO | WO00/50573 A1 | 8/2000 | |

OTHER PUBLICATIONS

Afeyan et al., *J. Chromatogr.*, 519, 1–29 (1990).
Haruna et al., *Virology*, 13, 264–267 (1961).
Huyghe et al., *Human Gene Therapy*, 6, 1403–1416 (1995).
Klemperer et al., *Virology*, 9, 536–545 (1959).
Philipson, *Virology*, 10, 459–465 (1960).
Shabram et al., *Human Gene Therapy*, 8, 454–456 and 458–461 (1997).

* cited by examiner

*Primary Examiner*—Mary E. Mosher
(74) *Attorney, Agent, or Firm*—Leydig, Voit & Mayer, Ltd.

(57) ABSTRACT

A method of enriching a solution of an adenovirus comprising applying a mixed solution comprising an adenovirus and at least one undesired type of biomolecule to an anion exchange chromatography resin containing a binding moiety selected from the group consisting of dimethylaminopropyl, dimethylaminobutyl, dimethylaminoisobutyl, and dimethylaminopentyl and eluting the adenovirus from the chromatography resin. Also provided is a method of purifying an adenovirus from adenovirus-infected cells comprising lysing such cells, applying the lysate to a single chromatography resin, eluting the adenovirus from the chromatography resin, and collecting a fraction containing adenovirus that is substantially as pure as triple CsCl density gradient-purified adenovirus. The present method further provides a method of accurately quantifying the number of adenoviral particles in a solution of adenovirus comprising applying to and eluting from an anion exchange chromatography resin a sample solution of adenovirus, comparing the absorbance of the sample solution of adenovirus and the absorbance of a standard solution of adenovirus, and quantifying the number of adenoviral particles in the sample solution.

30 Claims, 6 Drawing Sheets

EFFICIENT PURIFICATION OF ADENOVIRUS

This application claims priority to U.S. Provisional Patent Application Ser. No. 06/082,628, filed Apr. 22, 1998.

TECHNICAL FIELD OF THE INVENTION

The present invention relates to the efficient purification of adenovirus.

BACKGROUND OF THE INVENTION

Traditionally, adenoviral particles have been isolated through the use of density gradient purification protocols, such as through the use of cesium chloride (CsCl) gradients. While suitable for small-scale preparations, density gradient purification is tedious and time consuming and can not be easily scaled-up. Accordingly, the process is frequently considered commercially undesirable.

An alternative method for purifying adenovirus is to use column or batch chromatography. Early attempts to isolate viral particles by chromatographic techniques using diethylaminoethyl (DEAE) chromatography resins were first reported from 1959 to 1961. Haruna et al. (*Virology* 13: 264–267 (1961)) reported using DEAE ion exchange chromatography for purification of types 1, 3, and 8 adenoviruses, while Klemperer and Pereira (*Virology* 9: 536–545 (1959)) and Philipson (*Virology* 10: 459–465 (1960)) reported difficulties using the same method with other types of adenoviruses. These techniques were not widely used after about 1965, most likely as a result of the tendency of the chromatographic matrix to collapse during use. In addition, the selectivity of the chromatography resins available at the time made chromatographic purification of viruses inferior to the density gradient purification techniques.

Recently, there has been renewed interest in purifying viruses by chromatography. For example, Shabram et al. (WO 96/27677) and Huyghe et al. (*Human Gene Therapy* 6: 1403–1416 (1995)) disclose methods of using chromatography resins to purify viruses. Newer packing materials for chromatography also have been developed in the last decade and a half. These packing materials can be classified in four groups: (i) homogeneous cross-linked polysaccharides, which include soft gels (e.g., agarose) having good capacity, but poor resolution and a tendency to compress; (ii) macroporous polymers based on synthetic polymers, which include perfusion chromatography resins with large "throughpores," allowing for better diffusivity and leading to improved column efficiency, speed, and resolution; (iii) "tentacular" sorbents, which have tentacles that were designed for faster interactions with proteins (e.g. fractogel); and (iv) materials based on a soft gel in a rigid shell, which exploit the high capacity of soft gels and the rigidity of composite materials (e.g., Ceramic HyperD™ F) (see Boschetti, *J. Chromatogr.* 658: 207 (1994); Rodriguez, *J. Chromatogr.* 699: 47–61 (1997)).

It is desirable to increase the speed, ease of use, and efficiency of purification, particularly large-scale commercial purification, of these prior art techniques. The present invention provides such a process for purification of adenovirus. These and other advantages of the present invention, as well as additional inventive features, will be apparent from the description of the invention provided herein.

BRIEF SUMMARY OF THE INVENTION

The present invention provides a method of enriching a solution of an adenovirus. The method comprises: (i) obtaining a mixed solution comprising adenovirus and at least one undesired type of biomolecule; (ii) applying the mixed solution to an anion exchange chromatography resin containing a binding moiety selected from the group consisting of dimethylaminopropyl, dimethylaminobutyl, dimethylaminoisobutyl, and dimethylaminopentyl; and (iii) eluting the adenovirus from the purification chromatography resin with an eluant. The method can further comprise applying the mixed solution comprising adenovirus and at least one undesired type of biomolecule to an anion exchange pre-resin prior to applying the adenovirus to the anion exchange chromatography resin.

The present invention also provides a method of purifying an adenovirus from cells infected with adenovirus. The method comprises lysing cells infected with adenovirus, applying the lysate to a single chromatography resin, eluting the adenovirus from the chromatography resin, and collecting a fraction containing adenovirus, wherein the adenovirus is substantially as pure as triple CsCl density gradient-purified adenovirus.

The present invention further provides a method of accurately quantifying the number of adenoviral particles in a solution of adenovirus, such as a solution obtained from a crude lysate from cells infected with adenovirus, comprising (i) applying to and eluting from an anion exchange chromatography resin containing a binding moiety selected from the group consisting of dimethylaminopropyl, dimethylaminobutyl, dimethylaminoisobutyl, and dimethylaminopentyl a sample solution of adenovirus, (ii) determining the absorbance of the sample solution of adenovirus eluted from the chromatography resin and the absorbance of a standard solution of adenovirus, (iii) comparing the absorbance of the sample solution of adenovirus eluted from the chromatography resin with the absorbance of the standard solution of adenovirus, and quantifying the number of adenoviral particles in the sample solution.

The invention may best be understood with reference to the accompanying drawings and in the following detailed description of the preferred embodiments.

DESCRIPTION OF THE PREFERRED EMBODIMENTS

The present invention is directed to a method of enriching a solution comprising an adenovirus. By "adenovirus" is meant naturally occurring adenovirus and recombinant adenovirus, wherein the recombinant adenovirus can be infectious or noninfectious. The method comprises obtaining a mixed solution comprising adenovirus and at least one undesired type of biomolecule. By "biomolecule" is meant any macromolecule, for example, any protein, carbohydrate, lipid or nucleic acid (e.g., DNA and RNA) and the like, as well as fragments thereof. As used herein, "solution" is given that meaning normally ascribed to it in the art and is intended also to encompass a cell lysate. Any solution comprising adenovirus can be enriched in accordance with the present inventive method. A mixed solution of adenovirus ordinarily will be obtained by infecting eukaryotic cells with an adenovirus as defined herein, maintaining the cells for a period of time sufficient to amplify the number of adenoviral particles, collecting the infected cells, and lysing (breaking open) them in a buffered solution.

"Enriching" and "purifying," as well as "enriched" and "purified," are used interchangeably herein to indicate that the concentration of adenovirus in a given volume of solution is increasing or has increased, respectively. Desirably, the enriched or purified solution of adenovirus is substantially as pure as triple CsCl density gradient-purified adenovirus.

When purifying the virus from infected cells, i.e., eukaryotic cells, it is preferable not to let the infection proceed to the point where the virus itself causes lysis of the cells, because under these conditions individual cells lyse at substantially different times and degradative enzymes released by the lysed cells will begin to attack the released virus. Additionally, the strains on cellular metabolism just prior to adenoviral mediated cell lysis can cause a reduction in the accuracy of viral replication. Therefore, it is preferable to lyse the cells prior to adenoviral mediated lysis.

Any suitable method for lysis can be used. For example, the cells and culture medium can be centrifuged and the medium replaced with a solution of strong detergents and other additives (e.g., Triton™ X-100, Tween 20, Tween 80, or deoxycholate) and, after incubation for a suitable period of time, the sample can be collected for further processing. Alternatively, the cells can be collected by gentle centrifugation to form a cell pellet and lysed by freezing and thawing three times. A preferred alternative technique is to use a French press, or even more preferably, a microfluidizer. French presses and microfluidizers efficiently lyse eukaryotic cells by applying shear forces to rupture the cell membranes. The shear force process is more rapid and reproducible than other suitable methods for obtaining a solution comprising an adenovirus from an infected population of cells, i.e., eukaryotic cells. Accordingly, a mixed solution comprising an adenovirus and at least one undesired type of biomolecule for purification or enrichment in accordance with the present inventive methods can be obtained by microfluidizing a population of adenovirus-infected cells.

Once the solution from which the adenovirus is to be purified is obtained, it optionally can be clarified. If desired, such clarification can be performed by a moderately gentle centrifugation step to remove very large pieces of cell debris and larger unruptured organelles (if present). The cell lysate also can be clarified by filtration. Particularly, the cell lysate can be clarified and concentrated by tangential flow filtration (TFF) in accordance with methods known in the art. The solution can optionally then be treated with an enzyme capable of digesting DNA and RNA (a "DNase/RNase") to remove any DNA or RNA in the clarified cell lysate not contained within the adenoviral particles.

After the cell lysate is clarified, it optionally can be chromatographed on an anion exchange pre-resin prior to purification. Any suitable anion exchange chromatography resin can be used in the pre-resin. Preferably, the anion exchange chromatography resin to be used in the pre-resin has a surface group derivatized with a tertiary or quaternary amine (e.g., diethylaminoethyl, trimethylaminoethyl, or trimethylaminopropyl). The surface group can be linked to a matrix support through any suitable linker group as is known in the art. Acrylic polymer linkers are among those suitable for use in the context of the present invention. The support matrix can be composed of any suitable material; however, it is preferable for the matrix support to be a material based on the concept of "soft gel in a rigid shell." This "gel-filled" chromatography resin allows one to take advantage of the high capacity of soft gels, e.g., agarose, and the rigidity of composite materials for high flow rates and increased tolerance to compression or shrinking and swelling of the media, a common characteristic of soft gels. These "gel-filled" chromatography resins are well-known in the art and are described in U.S. Pat. Nos. 5,268,097 and 5,672,276, for example.

A desirable pre-resin anion exchange chromatography resin in the context of the present invention is Q Ceramic HyperD™ F, commercially available from BioSepra, Villeneuve-La-Garenne, France. Q Ceramic HyperD™ F is composed of a highly porous ceramized bead material filled with a functionalized flexible hydrophilic hydrogel, with an average bead size of $50\mu$ (with a particle range from $25-75\mu$). Q Ceramic HyperD™ F has a dynamic capacity of at least 85 mg/ml of bovine serum albumin (BSA) at 200 cm/hr with 50% breakthrough and of at least 80 mg/ml BSA at 600 cm/hr with 50% breakthrough. Due to the gel-filled nature of Q Ceramic HyperD™ F, there is a greater external surface area available for binding, compared to classical porous media, for which typically at least 50% of the exterior of the particle is composed of the pore entrance, where no binding occurs. As a result, 100% of the total external surface area of Q Ceramic HyperD™ F contributes to binding. This feature makes this chromatography resin a preferred pre-resin material.

Alternatively, the cell lysate optionally can be chromatographed on an expanded bed adsorption anion exchange pre-resin. For example, an expanded bed adsorption anion exchange chromatography resin with binding moieties derivatized with a quaternary amine (e.g., trimethylaminomethyl or DEAE) can be used. Expanded bed anion exchange chromatography resins are characterized by larger bead size, e.g., greater than 30μ in diameter, but usually not exceeding 500μ in diameter. Because of the large bead size, large fragments of cell debris and whole (unlysed) cells are able to flow freely through the chromatography resin (and its appropriate sized frit). Suitable expanded bed adsorption chromatography resins include, but are not limited to, Streamline QXL® (Pharmacia, Uppsala, Sweden) and DEAE Cellthru-Big Beads™ (Sterogene, Carlsbad, Calif., or the equivalent from UpFront Chromatography, Copenhagen, Denmark).

The cell lysate is eluted from the anion exchange pre-resin chromatography resin in any suitable eluant (e.g., 600 mM NaCl). The solution is suitably diluted, if necessary, to lower the concentration of the elution agent or other agents in the elution buffer. The semi-purified and concentrated cell lysate solution then can be applied to a suitable anion exchange chromatography resin for purification.

In view of the above, the present invention provides a method of enriching a solution for an adenovirus. The method comprises: (i) obtaining a mixed solution comprising adenovirus and at least one undesired type of biomolecule; (ii) applying the mixed solution to an anion exchange chromatography resin; and (iii) eluting the adenovirus from the chromatography resin with an eluant, such that an enriched solution of adenovirus is obtained. In addition, the mixed solution of adenovirus optionally can be clarified by tangential flow filtration. Further, the clarified mixed solution of adenovirus optionally can be chromatographed using an anion exchange pre-resin.

In this regard, the present invention also provides a method of purifying an adenovirus from cells infected with adenovirus. This method comprises lysing cells infected with adenovirus, applying the lysate to a single chromatography resin such that the adenovirus binds to the chromatography resin, eluting the adenovirus from the chromatography resin, and collecting a fraction containing the adenovirus. The adenovirus in the fraction is substantially as pure as triple CsCl density gradient-purified adenovirus.

Any suitable single chromatography resin can be used to purify the adenovirus from a cell lysate. Any suitable anion exchange chromatography resin having a surface group selected from the group consisting of dimethylaminopropyl, dimethylaminobutyl, dimethylaminoisobutyl, and dimethylaminopentyl can be used to purify the adenovirus from a mixed solution comprising adenovirus and at least one undesired type of biomolecule. The surface group is preferably dimethylaminopropyl. The surface group can be linked to a matrix support through any suitable linker group as is known in the art. Sulphonamide and acrylate linkers are among those suitable in the context of the present invention. The matrix support can be composed of any suitable material; however, it is preferable for the matrix support to be a perfusive anion exchange chromatography resin such that intraparticle mass transport is optimized.

Typical perfusive chromatography resins have large (e.g., 6,000–8,000 Å) pores that transect the particles. A network of smaller pores, thereby limiting diffusional pathlengths, enhances the surface area of the large-pore diameters. In part due to the bimodal distribution of pore sizes, the mobile phase and adenovirus enter and flow through the chromatography resin particles, utilizing both convective and diffusional transport. Such perfusive chromatography resins are well-known in the art and, for example, are more fully described by Afeyan et al. (*J. Chromatogr.* 519: 1–29 (1990), and U.S. Pat. Nos. 5,384,042; 5,228,989; 5,552,041; 5,605,623; and 5,019,270).

A suitable perfusive anion exchange chromatography resin in the context of the present invention is POROS® 50D, commercially available from PerSeptive Biosystems, Framingham, Massachusetts. POROS® 50D is a macroporous styrene-divinylbenzene copolymer chromatography resin that has a dynamic capacity of at least 100 mg/ml bovine serum albumin (BSA) at 100 cm/hr with 50% breakthrough and of at least 80 mg/ml BSA at 1000 cm/hr with 5% breakthrough. POROS® 50D exhibits a pressure drop of less than 3 bars at 1000 cm/hr in a 10 cm chromatography resin bed and the nominal particle size of the chromatography resin is about 50 microns (i.e., the average particle size is between 25 and 100 microns).

Anion exchange chromatography resins can be used either as "batch" chromatography resins or, preferably, as "flow-through" setups, preferably in the form of a column, especially for perfusive chromatography resins. Moreover, the present invention, in distinct contrast to prior art methods, provides for a fully scalable, simple, and rapid purification of adenovirus using chromatography.

An adenovirus purified in accordance with the present inventive method does not have a substantially lower particle to pfu ratio (pu/pfu) than a CsCl density gradient-purified adenovirus. That is, the pu/pfu of the purified adenovirus is at least 50% that of the CsCl density gradient-purified adenovirus, preferably, at least about 85% that of the CsCl density gradient-purified adenovirus, and more preferably, at least about 96% that of the CsCl density gradient-purified adenovirus. Moreover, the purity of the chromatographed adenovirus preferably exceeds that of an identical solution of adenovirus that is analytically indistinguishable from adenovirus purified through standard prior art triple CsCl density gradient purification (i.e., is as substantially pure as triple CsCl density gradient-purified adenovirus, e.g., is at least 90% as pure, preferably is at least 97% as pure, and more preferably is at least 99% as pure as triple CsCl gradient-purified adenovirus).

The adenovirus is substantially and suitably enriched in a solution by eluting it from the anion exchange chromatography resin in a suitable eluant. Typical suitable eluants are ionic in character such that they compete with the adenovirus for binding to the chromatography resin. The eluant is preferably applied to the chromatography resin in a discontinuous gradient, i.e., in two or more steps, or in a continuous gradient. Such gradients can be linear, concave, or convex. A suitable eluant is sodium chloride in a buffered solution. For example, adenovirus elutes from Q Ceramic Hyper D® F chromatography resin at between about 360 and about 475 mM NaCl, more particularly at about 415 mM NaCl, and from POROS® 50D chromatography resin at between about 360 and about 450 mM NaCl, more particularly at about 400 mM NaCl.

The anion exchange chromatography resin can be advantageously loaded in high concentrations of elution agents (e.g., at least about 75% of the concentration that is necessary to elute the adenovirus from the chromatography resin, preferably between about 85% to about 90% of the concentration that is necessary to elute the virus from the chromatography resin). By loading the anion exchange chromatography resin in high concentrations of eluting agent, certain impurities do not bind to the resin.

Elution of the enriched adenovirus can occur at any suitable flow rate. Typical flow rates for anion exchange chromatography resin used in the pre-resin are from about 100 cm/hr to about 1,000 cm/hr, preferably from about 200 cm/hr to about 500 cm/hr. Exemplary flow rates for anion exchange chromatography resin containing a binding moiety selected from the group consisting of dimethylaminopropyl, dimethylaminobutyl, dimethylaminoisobutyl, and dimethylaminopentyl are from about 100 cm/hr to about 1,500 cm/hr, preferably from about 500 cm/hr to about 1,250 cm/hr.

In order to accurately quantify the number of adenoviral particles either in a sample solution of adenovirus, such as a solution obtained from crude lysate from cells infected with adenovirus, a sample solution of an adenovirus can be prepared as described previously. The sample solution of adenovirus then can be enriched and purified by applying to and eluting from an anion exchange chromatography resin the sample solution of adenovirus as described previously. The absorbance of the sample adenovirus eluted from the chromatography resin is then determined. For comparison, the absorbance of a standard solution of adenovirus, i.e., a solution of adenovirus of known concentration, is determined. Through a comparison of the absorbance of the sample solution and the absorbance of the standard solution, the concentration of adenoviral particles, i.e., the number of adenoviral particles in a given volume, in a sample solution is determined.

The standard absorbance can be a single standard absorbance or a series or group of standard absorbance indicative of a range of concentrations of adenovirus. The sample absorbance and standard absorbance can be presented in similar or different (though preferably similar) formats, measurements, or units as long as a useful comparison can be performed. For example, a suitable standard absorbance can be an absorbance that is determined from a standard solution of adenovirus that has been treated in the same manner as a sample solution of adenovirus has been treated in accordance with the present inventive methods.

Quantification of the number of adenoviral particles is accomplished by comparing the sample absorbance to the standard absorbance in any suitable manner. For example, sample absorbance and standard absorbance can be compared by calculating a standard curve of the area under the peak corresponding to the virus elution from the chromatography resin on an absorbance versus time chromatograph. The absorbance of different known concentrations of adenovirus can be plotted on a graph, creating a standard curve. Using linear regression analysis, the sample concentration then can be determined.

Adenovirus enriched in a solution or purified from cells infected with adenovirus using anion exchange chromatography resins can be obtained in solutions that can contain high concentrations of an elution agent, e.g., NaCl. The buffer composition can be readily changed by any suitable technique to any desired buffer, e.g., a sterile, isotonic buffer for mammalian injection (e.g., lactated Ringer's solution) containing suitable excipients (stabilizers and cryopreservants) for long term storage of the purified adenovirus. Suitable techniques for changing the buffer composition include, but are not limited to, dialysis, diafiltration, and size exclusion chromatography. Suitable size exclusion chromatography matrices include Toyopearl HW-40C and Toyopearl HW40F (TosoHaas, Montgomeryville, Pa.); Uniflow™, Superflow™, and Ultraflow™ (Sterogene, Carlsbad, Calif.); Shodex™ (Thomson Instruments, Chantilly, Va.); and Bio-Sil™ and Bio-Gel™ (Bio-Rad, Hercules, Calif.). Each of these chromatography resins has a suitably low protein binding potential.

The present invention is further described in the following examples. These examples serve only to illustrate the invention and are not intended to limit the scope of the invention in any way.

EXAMPLES

Example 1

This example demonstrates purification of adenovirus from crude cell lysate. Purification was accomplished by first clarifying the cell lysate, applying the cell lysate to and eluting the cell lysate from an anion exchange pre-resin, and finally, applying the cell lysate to and eluting the cell lysate from an anion exchange resin containing a binding moiety selected from the group consisting of dimethylaminopropyl, dimethylaminopentyl, dimethylaminoisobutyl, and dimethylaminopentyl.

AdSEAP and AdVEGF$_{121}$ are adenoviral vectors with deletions in the E1 and E3 regions of the adenoviral genome containing a gene expression cassette, in this case, a cytomegaloviral (CMV) promoter operably linked to a foreign gene (transgene), e.g., secretory alkaline phosphatase (AdSEAP) or vascular endothelial growth factor 121 (AdVEGF$_{121}$), in the E1 region of the adenoviral genome. AdSEAP and AdVEGF$_{121}$ were propagated in spinner flasks, roller bottles, shaker bottles, or bioreactors containing about $10^5$–$10^6$ 293 cells per ml in the presence or absence of serum in the growth medium.

The cells and media were processed by either of the following two methods prior to any chromatography: (a) cells were concentrated by centrifugation, resuspended in a suitable buffer (25 mM Tris, pH 7.8, 75 mM NaCl, 10 mM MgCl$_2$) for optimal activity of the DNase/RNase, lysed in a microfluidizer (Microfluidics, Newton, Mass.) according to the manufacturer's directions, and clarified by filtration; or (b) cells were directly lysed in a microfluidizer according to the manufacturer's directions, clarified by filtration, and concentrated and diafiltered into the suitable buffer described above by tangential flow filtration (TFF). In both methods, the clarified cell lysate was then treated with a DNase/RNase, such as Benzonase® (Nycomed Pharma A/S, Denmark), according to the manufacturer's instructions, and diluted into a suitable buffer for the anion exchange pre-resin.

Figure 1:
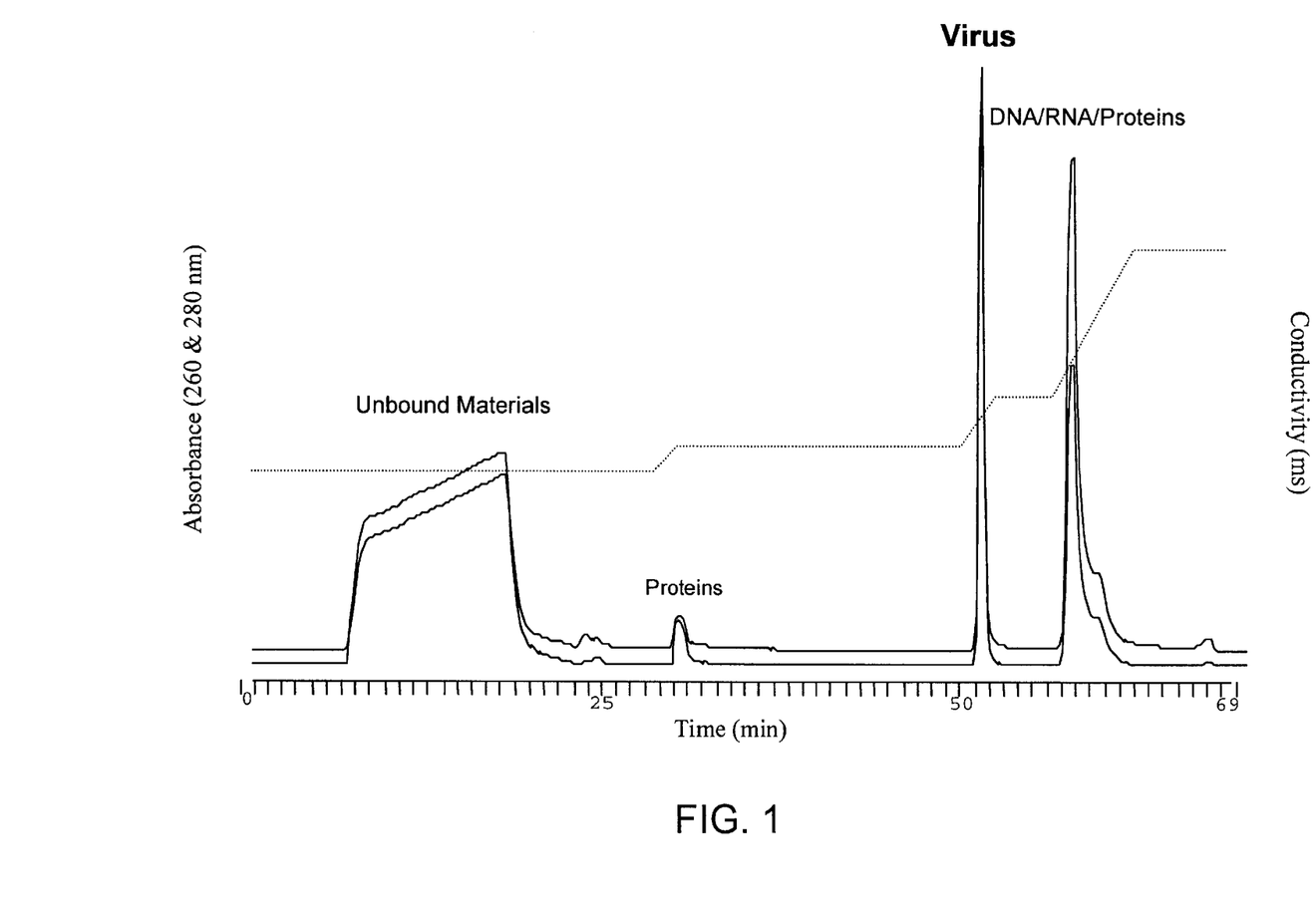
FIG. 1 is a chromatograph of adenovirally infected cell lysate eluted from a quaternary amine chromatography resin (Q Ceramic HyperD™ F), in which the y-axis depicts the absorbance (260 and 280 nm), the x-axis indicates time of elution (min), and the parallel y-axis (on the right) indicates the elution agent in the column as measured by conductivity (dashed line; ms).
Figure 2:
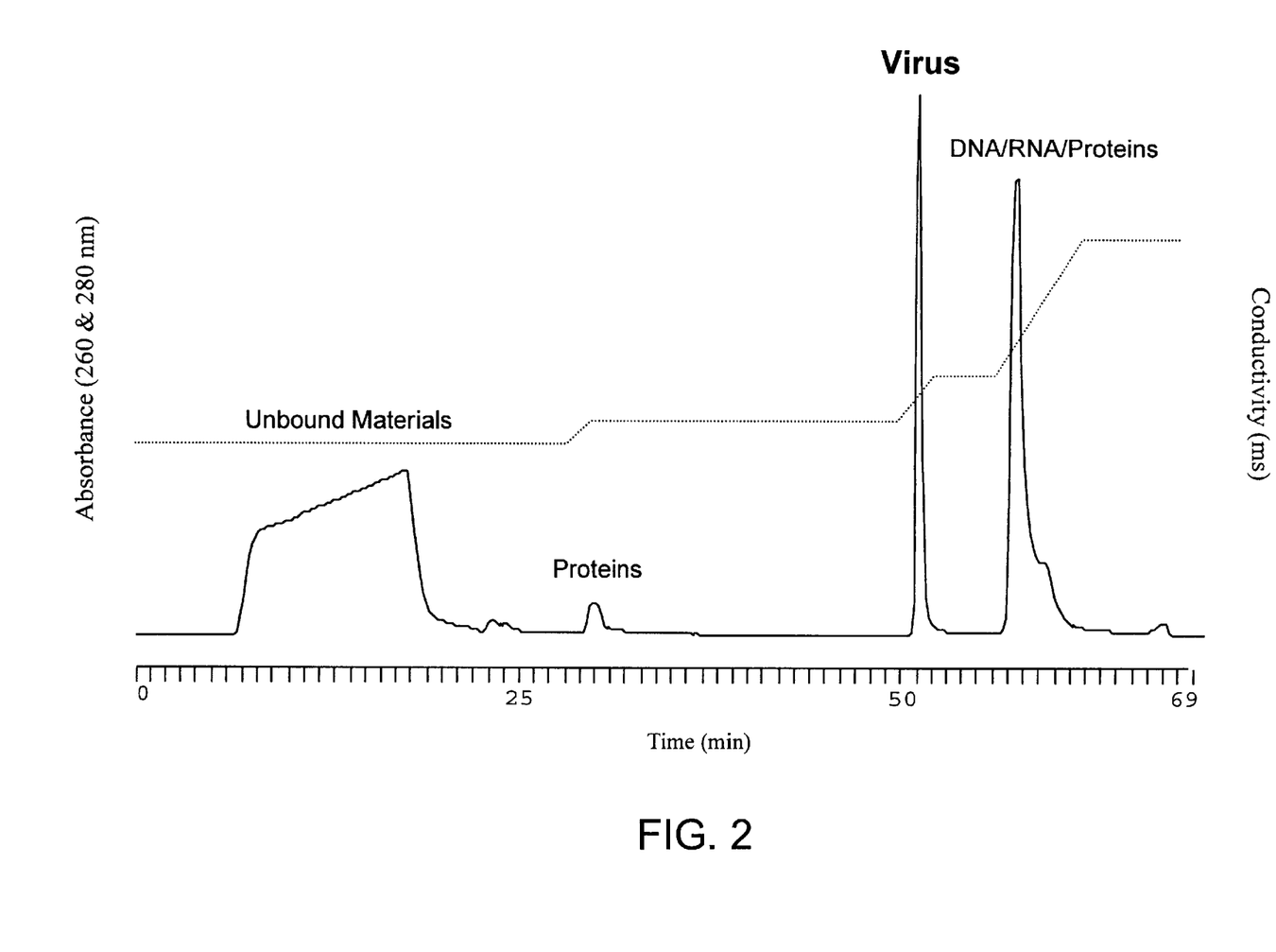
FIG. 2 is a chromatograph of adenovirally infected cell lysate clarified by tangential flow filtration, treated with a DNase/RNase (Benzonase®), and eluted from a quaternary amine chromatography resin (Q Ceramic HyperD™ F), in which the y-axis depicts the absorbance (260 and 280 nm), the x-axis indicates time of elution (min), and the parallel y-axis (on the right) indicates the elution agent in the column as measured by conductivity (dashed line; ms).

The cell lysate was then applied to a Q Ceramic HyperD™ F column and eluted with a step gradient of 360 to 475 mM NaCl. FIG. 1, which is a chromatograph of adenovirally-infected cell lysate eluted from a quaternary amine chromatography resin (Q Ceramic HyperD™ F column), shows the elution of the adenovirus from the anion exchange pre-column, Q Ceramic HyperD™ F, when the DNase/RNase step was not performed. The concentrated and partially purified viral peak, which elutes at about 415 mM NaCl when eluted with step gradients of 360, 450, and 1000 mM NaCl, was contained in one fraction around 51 minutes. FIG. 2, which is a chromatograph of adenovirally infected cell lysate clarified by tangential flow filtration, treated with DNase/RNase, and eluted from a quaternary amine chromatography resin, shows the elution of the adenovirus from the anion exchange pre-column, Q Ceramic HyperD™ F, when a DNase/RNase (Benzonase®) was used. A significant decrease in the magnitude of the nucleic acid peak eluting after the virus peak was observed.

The eluant from the anion exchange pre-column was then diluted by about 30%, which is necessary to dilute out the elution agent, in this case NaCl, to a concentration less than the elution concentration for the dimethylaminopropyl perfusive chromatography (POROS® 50D) column, which was used to complete the purification of the adenovirus from the crude cell lysate. The POROS® 50D column was loaded in a concentration of 300 mM NaCl. The column was then eluted with a step gradient of sodium chloride (360 mM to 450 mM).

A chromatograph of adenovirally infected cell lysate clarified by tangential flow filtration, treated with DNase/RNase, and eluted from a quaternary amine chromatography column and a dimethylaminopropyl perfusive chromatography column, shows elution of the adenovirus from the POROS® 50D column. Substantially, only one sharp peak at approximately 35 mins was obtained. Analytical characterization of the purified adenovirus indicated that the purity of the adenovirus was substantially indistinguishable from triple CsCl density gradient-purified adenovirus.

Therefore, adenovirus was purified from crude cell lysate by filtering the cell lysate, applying the cell lysate to and eluting the cell lysate from a quaternary amine column anion exchange pre-column, and finally, applying the cell lysate to and eluting the cell lysate from an anion exchange column containing a dimethylaminopropyl binding moiety.

Example 2

This example demonstrates purification of adenovirus from crude cell lysate. Purification was accomplished by first clarifying the cell lysate, applying the cell lysate to and eluting the cell lysate from an expanded bed adsorption anion exchange pre-column, and finally, applying the cell lysate to and eluting the cell lysate from an anion exchange column containing a binding moiety selected from the group consisting of dimethylaminopropyl, dimethylaminopentyl, dimethylaminoisobutyl, and dimethylaminopentyl.

Figure 3:
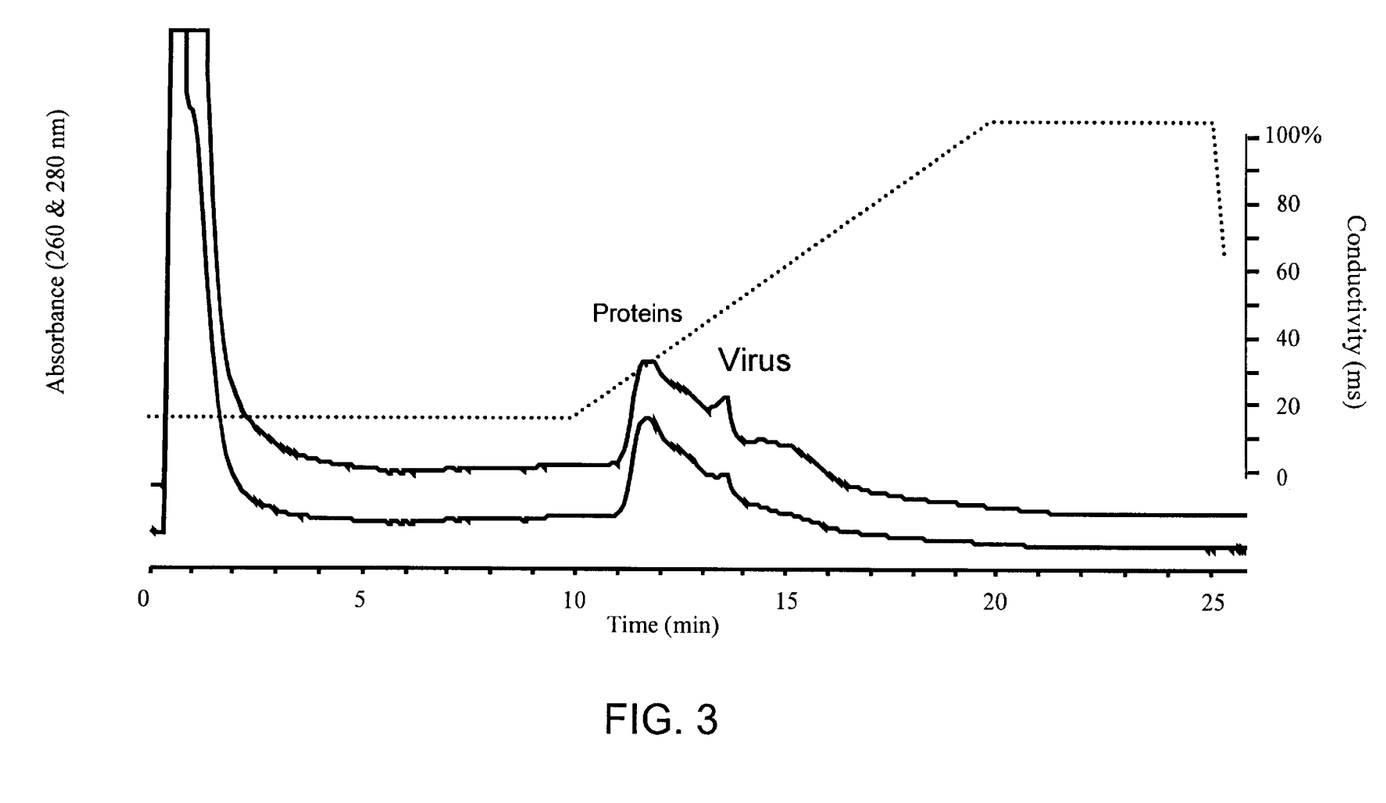
FIG. 3 is a chromatograph of adenovirally infected cell lysate eluted from an expanded bed adsorption chromatography resin (Streamline QXL®), in which the y-axis depicts the absorbance (260 & 280 nm), the x-axis indicates time of elution (min), and the parallel y-axis (on the right) indicates the elution agent in the column as measured by conductivity (dashed line) in millisienmmens (ms).

AdSEAP (the adenoviral vector as described in Example 1) was propagated in spinner flasks containing about $10^5$–$10^6$ 293 cells per ml. The cells and media were lysed in a microfluidizer according to the manufacturer's directions. The cell lysate was applied to a Streamline QXL® Expanded Bed Adsorption anion exchange pre-column (Pharmacia, Uppsala, Sweden) (to remove large debris and unlysed cells). The Streamline QXL® column also served partially to purify and concentrate the adenovirus. FIG. 3, which is a chromatograph of adenovirally infected cell lysate eluted from an expanded bed absorption chromatography resin, shows elution of the adenovirus from the Streamline QXL® column. The viral peak was contained in the fraction 14 (one fraction per minute) which eluted at about 600 mM NaCl. The eluant from the Streamline QXL® column was diluted about 1:2. The dilution was necessary to dilute out the elution agent, in this case NaCl, to a concentration less than the elution concentration for the POROS® 50D column, which was used next.

Figure 4:
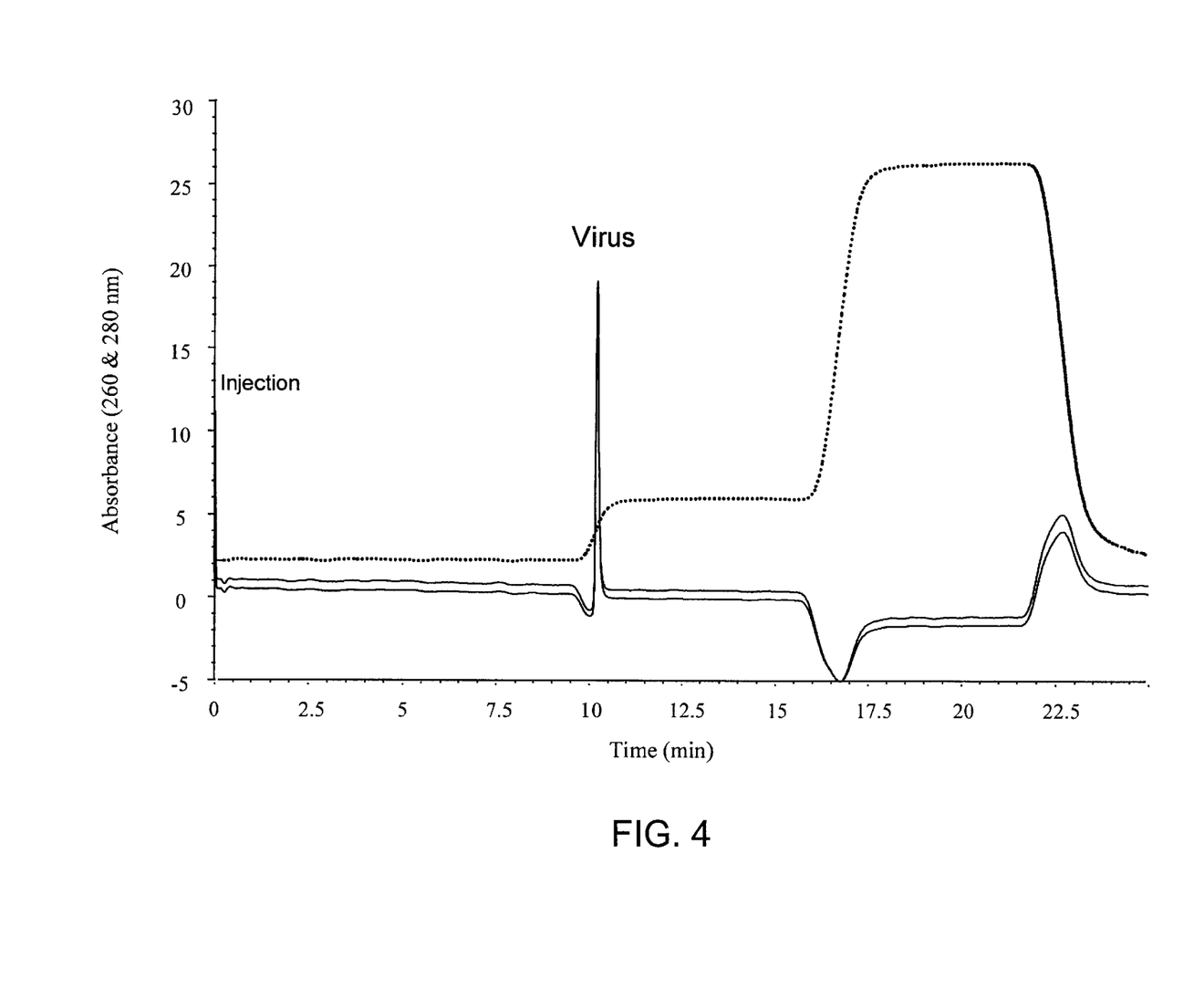
FIG. 4 is a chromatograph of adenovirally infected cell lysate purified by triple CsCl gradient centrifugation and quantified using a dimethylaminopropyl perfusive (POROS® 50D) analytical scale column, in which the y-axis depicts the absorbance (260 & 280 nm) and the x-axis indicates time of elution (min).

A POROS® 50D column was used to complete purification of the adenovirus. The POROS® 50D was loaded at a concentration of 300 mM NaCl. The column was then eluted with a linear gradient of sodium chloride (360 mM to 450 mM), wherein the adenovirus eluted from the POROS® 50D column. A chromatograph of adenovirally infected cell lysate eluted from an expanded bed absorption chromatography resin and a dimethylaminopropyl perfusive chromatography resin, shows substantially only one sharp peak at approximately 15 mins when eluted with a linear gradient of NaCl from 360 to 450 mM, such that the virus eluted at about 400 mM NaCl. Analytical characterization of the purified adenovirus indicated that the purity of the adenovirus was substantially indistinguishable from triple CsCl density gradient-purified adenovirus (see FIG. 4).

Therefore, adenovirus was purified from crude cell lysate by filtering the cell lysate, applying the cell lysate to and eluting the cell lysate from an expanded bed anion exchange pre-column, and finally, applying the cell lysate to and eluting the cell lysate from an anion exchange column containing a dimethylaminopropyl binding moiety.

Example 3

This example demonstrates—in distinct contrast to prior art methods—purification of an adenovirus by a single chromatography column from a crude cell lysate, wherein the purification was at least 95% as pure as triple CsCl density gradient-purified adenovirus. Additionally, this technique provides a rapid and accurate method to quantify the total number of viral particles in a crude lysate.

Figure 5:
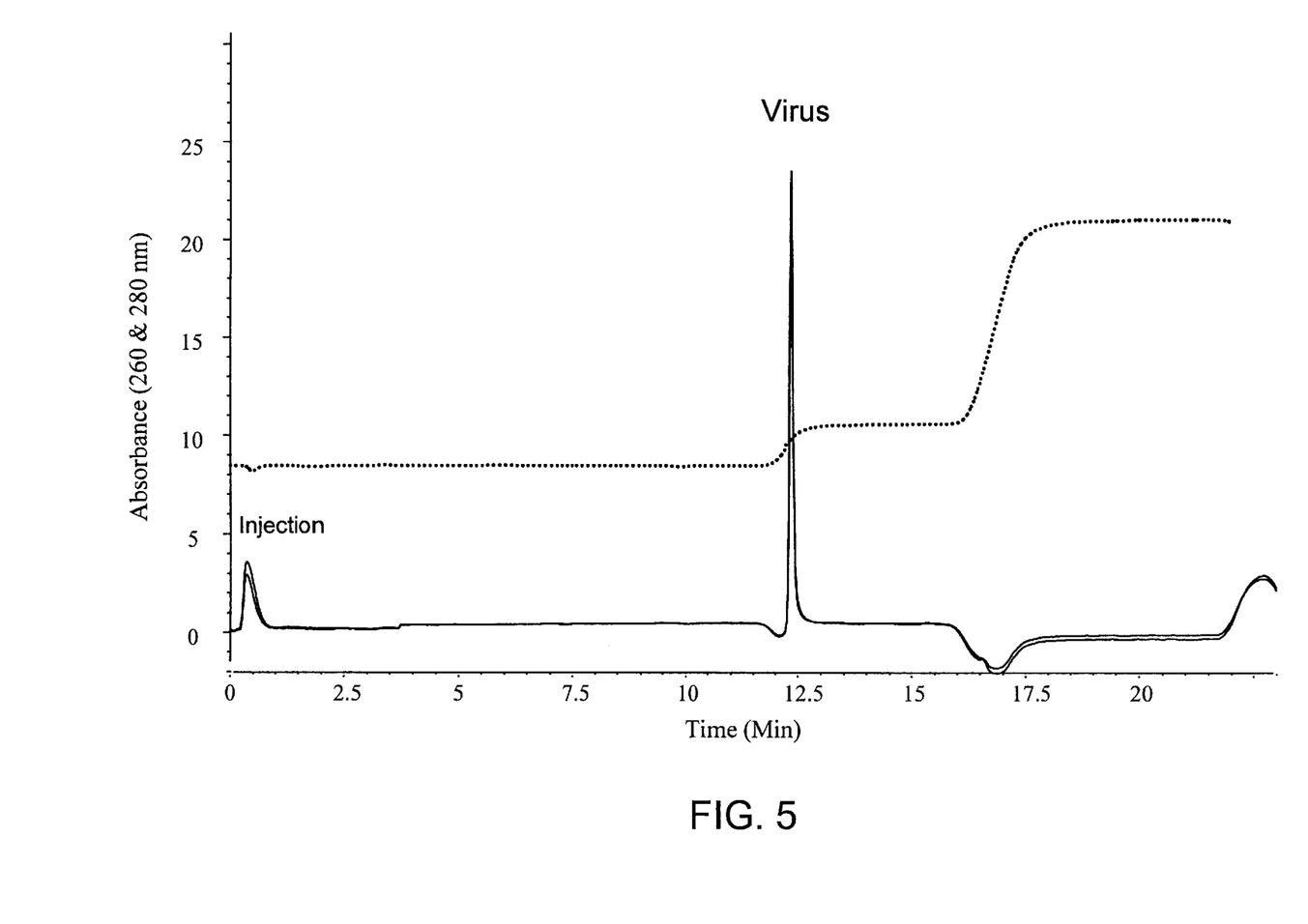
FIG. 5 is a chromatograph of adenovirally infected cell lysate eluted from an expanded bed adsorption chromatography resin (Streamline QXL®) and twice from a dimethylaminopropyl perfusive chromatography resin (POROS® 50D), in which the y-axis depicts the absorbance (260 & 280 nm) and the x-axis indicates time of elution (min).
Figure 6:
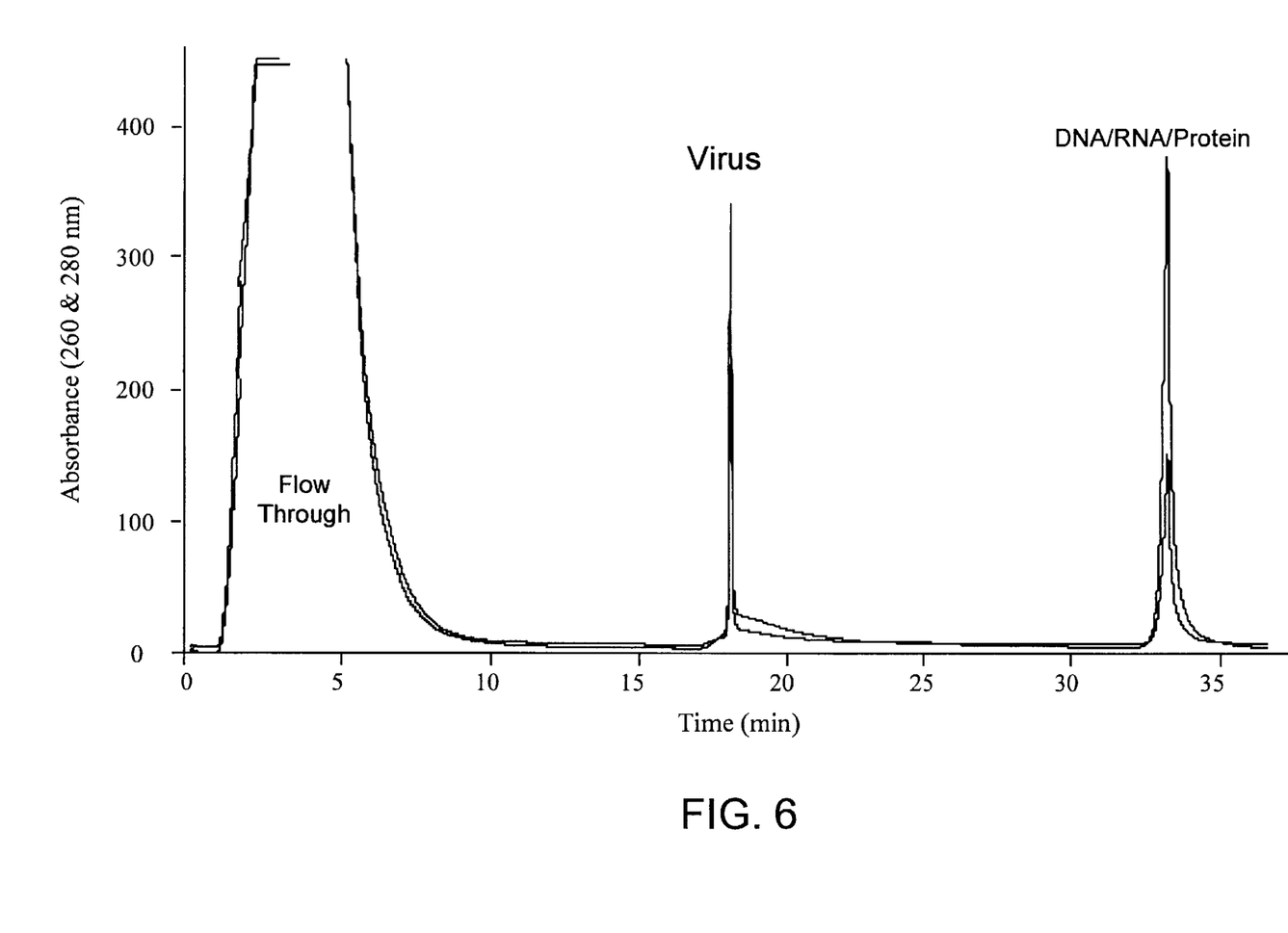
FIG. 6 is a chromatograph of adenovirally infected cell lysate eluted from a dimethylaminopropyl perfusive chromatography resin (POROS® 50D), in which the y-axis depicts the absorbance (260 and 280 nm) and the x-axis indicates time of elution (min).

AdSEAP (the adenoviral vector according to Example 1) was grown and lysed as in Example 1, method (a). The whole cell lysate was applied to a POROS® 50D column in 360 mM NaCl. The column was eluted as indicated in Example 1, resulting in the chromatograph of absorbance (260 nm and 280 nm) versus time (min) depicted in FIG. 6. Analytical examination of the peak fraction indicated that the purification was indistinguishable from triple CsCl density gradient-purified adenovirus (FIGS. 5 & 6), in which the top horizontal line is an inline measure of conductivity indicative of actual NaCl concentration. The substantial overlap and the ratio of the peak absorbance at 260 nm (the higher trace in the chromatograph) to 280 nm (the lower trace in the chromatograph), which was 1.27 (1.25±0.08 was the empirically determined ratio of pure virus), indicated that the virus was substantially pure. The lack of non-superimposed peaks (or secondary peaks) also indicated that the virus was substantially pure.

Various solutions of adenovirus of known concentration were applied to a POROS® 50D column in 360 mM NaCl. The column was eluted as indicated in Example 1, and the absorbance (260 & 280 nm) versus time of elution (min) was chromatographed. The area under the peak corresponding to the adenoviral elution was determined for each different concentration and plotted as a graph of area versus concentration of adenovirus. The area under the curve of the AdSEAP chromatograph in FIG. 6 corresponding to the adenoviral elution was calculated and compared to the standard curve using linear regression and determined that the crude lysate contained $4.64 \times 10^{10}$ pu/mL.

Thus, the present invention provides a single-step method for purifying adenovirus from a whole cell lysate. Therefore, adenovirus, which was at least 95% as pure as triple CsCl density gradient-purified adenovirus, was purified from crude cell lysate by a single chromatography column. Additionally, the total number of adenovirus in a crude cell lysate was rapidly and accurately quantified.

Example 4

This example demonstrates that the buffer composition of adenovirus isolated from anion exchange columns can be readily changed (e.g., from high salt concentration to low salt concentration).

About 0.1 column volumes (0.01 column volumes to about 0.25 column volumes) of the adenovirus-containing solution isolated in Example 1 was applied to a Toyopearl HW-40C column or a Uniflow 4 column equilibrated with a suitable sterile, isotonic buffer for mammalian injection (e.g., lactated Ringer's solution) and containing suitable excipients (stabilizers and cryopreservants) for long-term storage of the purified adenovirus. The column fraction containing the adenovirus was identified by in-line spectroscopy and retained. The purified virus was contained in a buffer containing about 10 mM Tris, pH 7.8, 75 mM NaCl, and various stabilizers.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of enriching a solution for an adenovirus comprising:
   (i) obtaining a mixed solution comprising an adenovirus and an undesired biomolecule;
   (ii) applying the mixed solution to an anion exchange chromatography resin comprising a binding moiety selected from the group consisting of dimethylaminopropyl, dimethylaminobutyl, dimethylaminoisobutyl, and dimethylaminopentyl, such that the adenovirus binds to the chromatography resin; and
   (iii) eluting the adenovirus from the chromatography resin with an eluant, such that an enriched solution of adenovirus is obtained.

2. The method of claim 1, wherein the binding moiety is dimethylaminopropyl.

3. The method of claim 1, wherein the eluant is a continuous or discontinuous gradient eluant.

4. The method of claim 2, wherein the eluant is a continuous or discontinuous gradient eluant.

5. The method of claim 1, wherein the eluant is a gradient eluant comprising a gradient of sodium chloride.

6. The method of claim 2, wherein the eluant is a gradient eluant comprising a gradient of sodium chloride.

7. The method of claim 1, wherein the anion exchange chromatography resin is a perfusive anion exchange chromatography resin.

8. The method of claim 2, wherein the anion exchange chromatography resin is a perfusive anion exchange chromatography resin.

9. The method of claim 1, wherein the mixed solution is obtained by microfluidizing a population of adenovirus-infected cells.

10. The method of claim 2, wherein the mixed solution is obtained by microfluidizing a population of adenovirus-infected cells.

11. The method of claim 1, wherein obtaining the mixed solution comprises:
   (a) applying a solution comprising an adenovirus and an undesired biomolecule to an anion exchange pre-resin, and
   (b) eluting the adenovirus from the pre-resin.

12. The method of claim 11, wherein the anion exchange pre-resin is a quaternary amine resin.

13. The method of claim 12, wherein the anion exchange pre-resin is an expanded bed adsorption resin.

14. The method of claim 2, wherein obtaining the mixed solution comprises:
   (a) applying a solution comprising an adenovirus and an undesired biomolecule to an anion exchange pre-resin, and
   (b) eluting the adenovirus from the pre-resin.

15. The method of claim 14, wherein the anion exchange pre-resin is a quaternary amine resin.

16. The method of claim 15, wherein the anion exchange pre-resin is an expanded bed adsorption resin.

17. The method of claim 11, wherein the solution applied to the anion exchange pre-resin in step (a) contains at least about 75% by concentration of an eluting agent required to elute the adenovirus from the anion exchange pre-resin.

18. The method of claim 17, wherein the solution applied to the anion exchange pre-resin in step (a) contains about 85% to about 90% by concentration of an eluting agent required to elute the adenovirus from the anion exchange pre-resin.

19. The method of claim 14, wherein the solution applied to the anion exchange pre-resin in step (a) contains at least about 75% by concentration of an eluting agent required to elute the adenovirus from the anion exchange pre-resin.

20. The method of claim 19, wherein the solution applied to the anion exchange pre-resin in step (a) contains about 85% to about 90% by concentration of an eluting agent required to elute the adenovirus from the anion exchange pre-resin.

21. The method of claim 1, wherein the method further comprises quantifying the number of adenoviral particles in the enriched solution by comparing the adsorption of the enriched solution to a standard solution containing a known number of adenoviral particles.

22. The method of claim 21, wherein the mixed solution is prepared from a crude cell lysate of adenovirus-infected cells.

23. The method of claim 21, wherein the binding moiety used in step (ii) of the method is dimethylaminopropyl.

24. The method of claim 23, wherein the mixed solution is prepared from a crude cell lysate of adenovirus-infected cells.

25. The method of claim 1, wherein the mixed solution applied to the anion exchange chromatography resin in step (ii) contains at least about 75% by concentration of an eluting agent required to elute the adenovirus from the anion exchange chromatography resin.

26. The method of claim 1, wherein the anion exchange chromatography resin comprises an acrylate or sulphonamide linker connected to the binding moiety.

27. The method of claim 26, wherein the anion exchange chromatography resin comprises a POROS® 50D resin.

28. The method of claim 11, wherein the pre-resin comprises an acrylate or sulphonamide linker.

29. The method of claim 28, wherein the pre-resin comprises a Streamline QXL resin.

30. The method of claim 11, wherein the pre-resin comprises a Q Ceramic HyperD™ F resin.

* * * * *